(12) United States Patent
Sudo

(10) Patent No.: US 7,594,435 B2
(45) Date of Patent: Sep. 29, 2009

(54) HUMIDITY SENSOR AND SEMICONDUCTOR DEVICE INCLUDING THE SAME

(75) Inventor: Minoru Sudo, Chiba (JP)

(73) Assignee: Seiko Instruments Inc., Chiba (JP)

( * ) Notice: Subject to any disclaimer, the term of this patent is extended or adjusted under 35 U.S.C. 154(b) by 127 days.

(21) Appl. No.: 11/654,416

(22) Filed: Jan. 17, 2007

(65) Prior Publication Data

US 2007/0186649 A1   Aug. 16, 2007

(30) Foreign Application Priority Data

Jan. 18, 2006   (JP) .............................. 2006-009908

(51) Int. Cl.
  *G01N 27/22*   (2006.01)
  *G01N 27/04*   (2006.01)
  *G01N 27/12*   (2006.01)

(52) U.S. Cl. ............... 73/335.04; 73/335.02; 73/335.05

(58) Field of Classification Search ............. 73/335.02, 73/335.03, 335.04, 335.05
See application file for complete search history.

(56) References Cited

U.S. PATENT DOCUMENTS

| 3,559,456 | A | * | 2/1971 | Lomker et al. ............. 73/29.05 |
| 4,845,421 | A | * | 7/1989 | Howarth et al. ............ 324/688 |
| 5,077,635 | A | * | 12/1991 | Bollhagen et al. ........... 361/287 |
| 5,767,867 | A | * | 6/1998 | Hu .............................. 345/561 |
| 6,765,793 | B2 | * | 7/2004 | Kehret et al. ................ 361/690 |
| 2005/0188764 | A1 | * | 9/2005 | Itakura et al. ............ 73/335.04 |
| 2006/0194332 | A1 | * | 8/2006 | Wado et al. ................ 436/151 |

FOREIGN PATENT DOCUMENTS

| JP | H08-145932 | 6/1996 |
| JP | 2003-156464 | 5/2003 |

\* cited by examiner

*Primary Examiner*—Daniel S Larkin
(74) *Attorney, Agent, or Firm*—Brinks Hofer Gilson & Lione

(57) ABSTRACT

Provided is a humidity sensor whose electrode is set to have an island-like configuration and is enclosed by a humidity sensitive film. As a result, in the humidity sensor, adhesion property between the humidity sensitive films on the electrode is enhanced and thus high reliability is achieved.

11 Claims, 5 Drawing Sheets

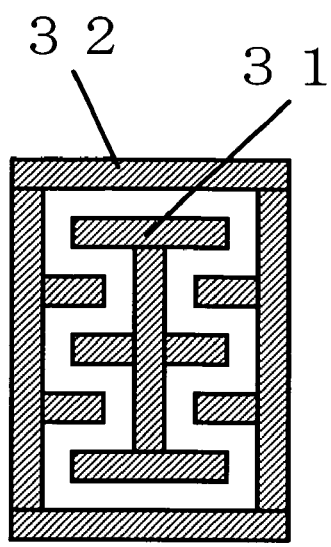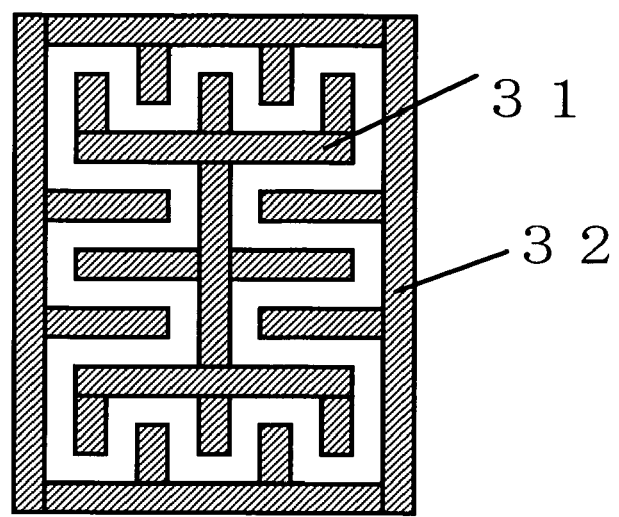
FIG. 3A  FIG. 3B

PRIOR ART

HUMIDITY SENSOR AND SEMICONDUCTOR DEVICE INCLUDING THE SAME

This application claims priority under 35 U.S.C. §119 to Japanese Patent Application No. JP2006-009908 filed Jan. 18, 2006, the entire content of which is hereby incorporated by reference.

BACKGROUND OF THE INVENTION

1. Field of the Invention

The present invention relates to a semiconductor humidity sensor.

2. Description of the Related Art

As a conventional capacitive humidity sensor, a circuit as shown in FIG. 5 has been known (see, for example, FIG. 1 of JP 2003-156464 A).

In FIG. 5, comb-shaped electrodes are formed on a substrate. The electrodes are coated thereon with a humidity sensitive film whose dielectric constant varies depending on humidity. The humidity sensitive films are inserted between the comb-shaped electrodes. An approximate capacitance C between the electrodes 21 and 22 can be obtained by the following equation (1):

$$C = \epsilon_0 \cdot \epsilon_H \cdot S / d_H \qquad (1)$$

where $d_H$ is an interval between electrodes 21 and 22, S is an area where the electrodes 21 and 22 are opposing each other, $\epsilon_H$ is a dielectric constant of the humidity sensitive film between the electrodes 21 and 22, and $\epsilon_0$ is the permittivity of vacuum.

Change in the dielectric constant $\epsilon_H$ of the humidity sensitive film between the electrodes on humidity causes change in the capacitance C between the electrodes 21 and 22, thus measurement of the capacitance C enables the measurement of humidity.

In addition, as a circuit similar to that of FIG. 5, a resistance type humidity sensor has been known (see, for example, FIG. 1 of JP 08-145932 A). In the resistance type humidity sensor, a humidity sensitive film whose resistivity varies depending on humidity is coated onto the electrodes 21 and 22 (between the electrodes 21 and 22), in place of the above-mentioned humidity sensitive film whose dielectric constant varies depending on the humidity. In this case, a resistance between the electrodes 21 and 22 varies depending on humidity, thus measurement of the resistance enables the measurement of humidity.

Poor adhesion property between the humidity sensitive films on the electrode and between the electrodes and the substrate in the conventional humidity sensor raises a problem of easy peeling off of the humidity sensitive film. In addition, there is a problem in that a humidity distribution in a minute area cannot be determined.

SUMMARY OF THE INVENTION

In order to solve the above-mentioned problems, the present invention has been made, and therefore, it is an object of the present invention to provide a humidity sensor in which adhesion property between humidity sensitive films on an electrode and between the electrodes and a substrate are enhanced, for exactly determining the humidity distribution in a small region.

A humidity sensor according to the present invention adopts an electrode structure in which a plurality of island-like unit cells is arranged in a grid pattern.

The humidity sensor according to the present invention exhibits enhanced adhesion property between the humidity sensitive films and has an enhanced reliability effectively

BRIEF DESCRIPTION OF THE DRAWINGS

In the accompanying drawings:

FIGS. 3A and 3B each show an electrode unit cell according to another embodiment of the present invention;

DETAILED DESCRIPTION OF THE PREFERRED EMBODIMENTS

In order to solve the above-mentioned problems, the present invention provides a novel electrode structure of a humidity sensor. In the following embodiments, the structure is described in detail.

First Embodiment

Figure 1:
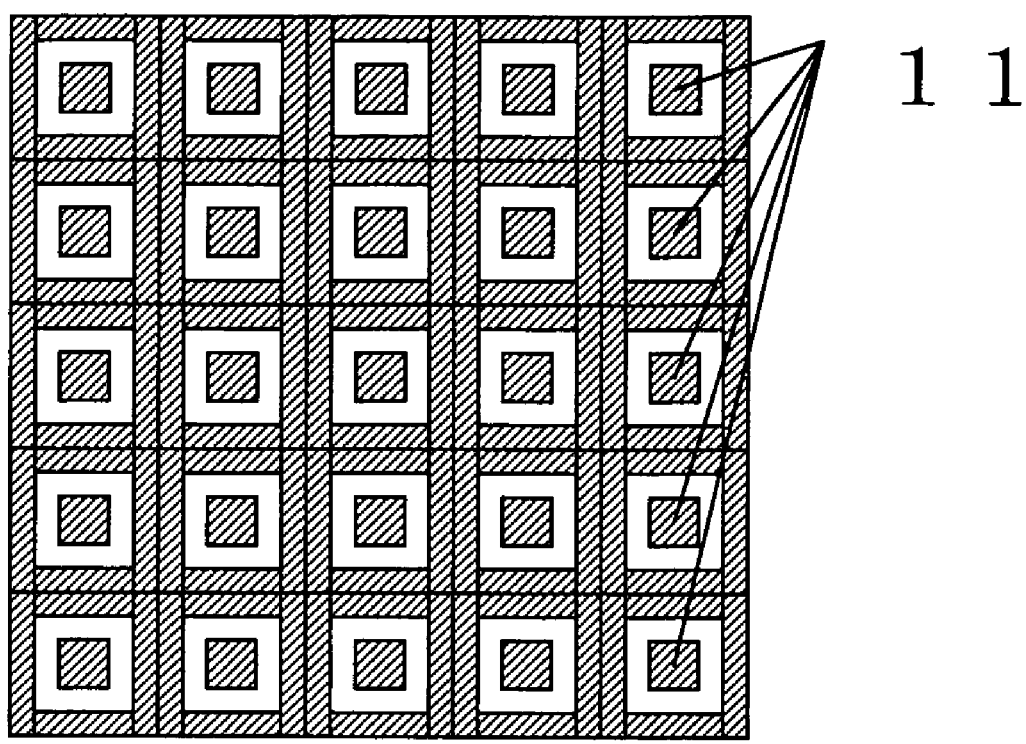
FIG. 1 shows electrodes of a humidity sensor according to a first embodiment of the present invention.

Description is given below on an embodiment of the present invention with reference to the drawings. FIG. 1 shows an electrode structure of a humidity sensor according to a first embodiment of the present invention. In this structure a plurality of island-like separate electrodes 11 is respectively enclosed by an outer electrode. In FIG. 1, basic electrode unit cells are arranged in a 5×5 grid pattern.

Figure 2A:
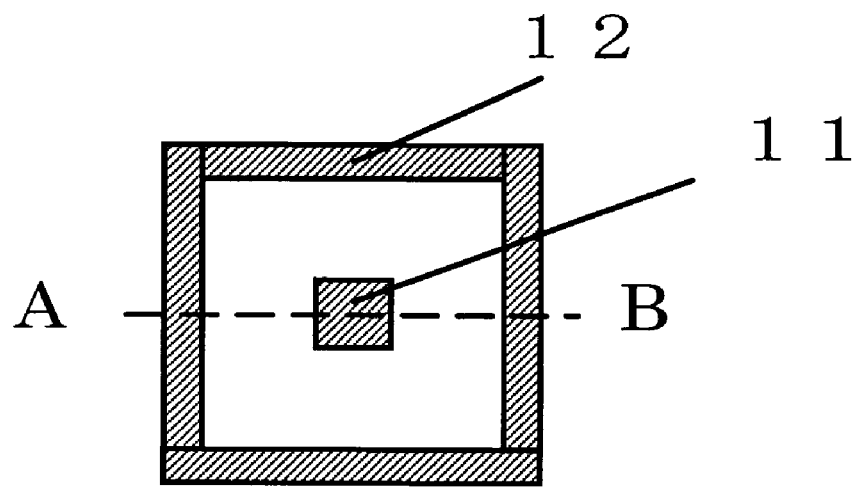
FIGS. 2A and 2B each show an electrode unit cell according to the first embodiment of the present invention.
Figure 2B:
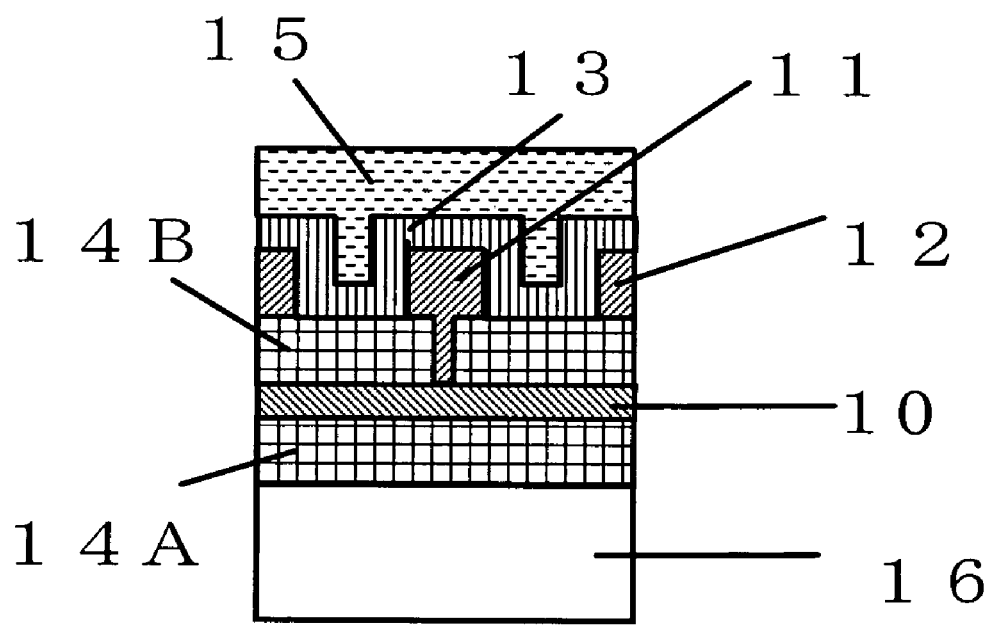

FIG. 2A shows a top view of the unit cell for electrode structure and FIG. 2B shows a sectional view thereof (taken along the line A-B of FIG. 2A). In FIG. 2A, a first electrode 11 and a second electrode 12 formed to enclose the electrode 11 are illustrated. A humidity sensitive film exists between the first electrode 11 and the second electrode 12. Measurement of a capacitance or a resistance between the electrodes 11 and 12 enables the measurement of the humidity. In the sectional view of FIG. 2B, a substrate 16 (e.g., semiconductor), an insulating film 14A, a first metal wiring layer 10, an insulating film 14B, the electrodes 11 and 12 formed of a second metal wiring layer, a protective film 13 (e.g., nitride film) for protecting the electrodes, and a humidity sensitive film 15 are disposed in the stated order from the bottom. The protective film 13 is formed on surfaces of the electrodes 11 and 12. The first electrode 11 formed of the second metal wiring layer is connected to the first metal wiring layer via a through-hole formed in the insulating film 14B.

If connection of all the electrodes 11 of the unit cells to the same first metal wiring layer is made, measurement of the capacitance or the resistance between the first metal wiring layer and the electrode 12 formed of the second metal wiring layer enables the measurement of the humidity.

Figure 5:
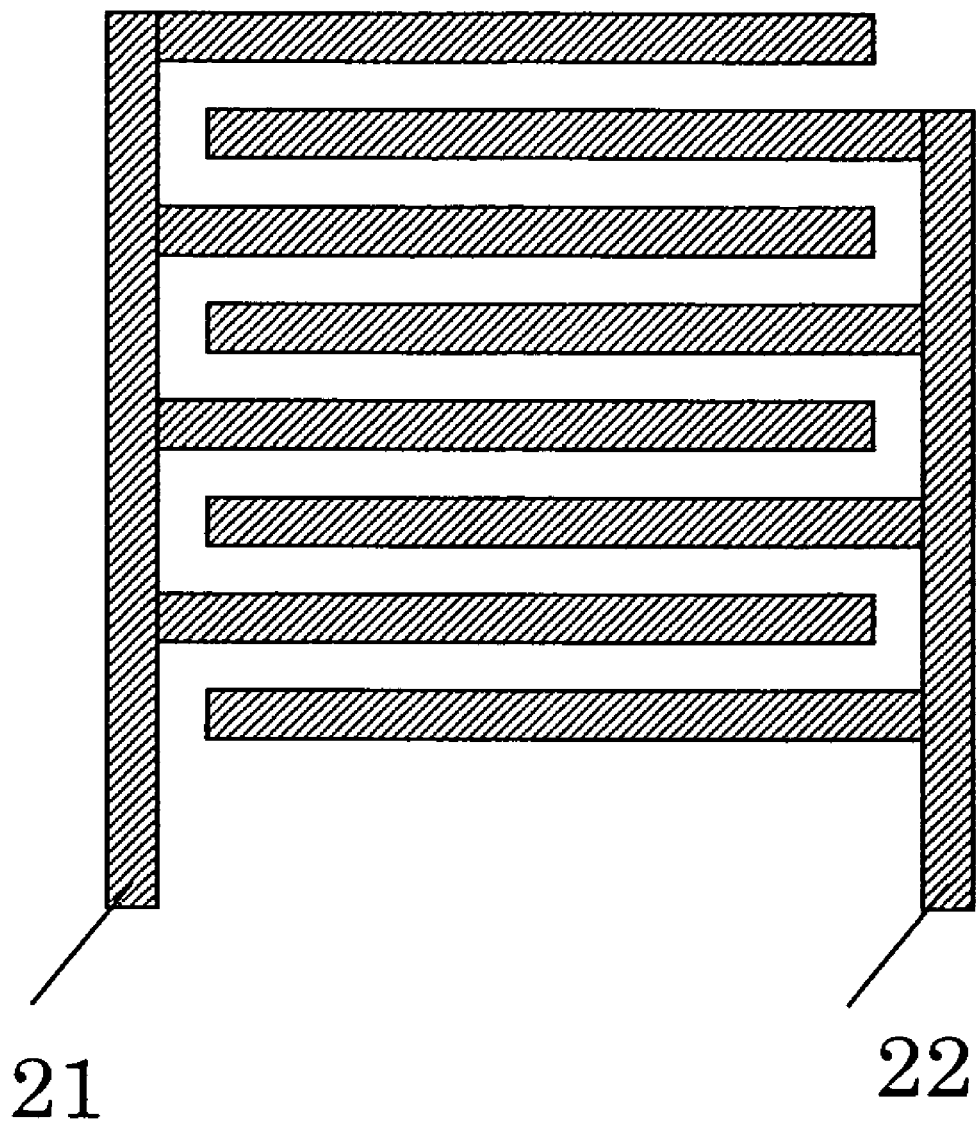
FIG. 5 shows electrodes of a conventional humidity sensor.

In the humidity sensor according to the present invention adoption of the electrode structure shown in FIG. 1 results in the significantly larger adhesion property between the humidity sensitive film and the electrodes than that of the conventional humidity sensor. In the conventional structure shown in FIG. 5, formation of comb-shaped electrodes in a lateral direction caused easy peeling-off of the humidity sensitive film along that direction. On the other hand, in the present invention, as shown in FIGS. 2A and 2B, formation of the unit from the island-like electrode 11 and the electrode 12 formed to enclose the electrode 11 enables the incorporation of the humidity sensitive film 15 to enclose the island-like electrode 11, leading to the humidity sensor having high reliability, which can avoid poor adhesion property in a certain direction such as the tooth direction in the comb-shaped electrode structure.

Further, FIGS. 2A and 2B show the square electrode 11 and the square electrode 12 enclosing the electrode 11 as a configuration of the unit cell. However, as shown in FIGS. 3A and 3B, a polygonal electrode 31 having projections and depressions and a polygonal electrode 32 having projections and depressions and enclosing the electrode 31 can enhance adhesion properties between the electrodes and the humidity sensitive film as in the case of FIGS. 2A and 2B.

Second Embodiment

In the first embodiment, the electrode 11 of the unit cell is connected to the same first metal wiring layer as an example. As shown in FIG. 1, when the plurality of unit cells is arranged, measurement of a capacitance or a resistance for each unit cell enables the measurement of the humidity of a local small region where the unit cell is included. Thus, a humidity distribution of the humidity sensor can be measured.

Using photolithography in a semiconductor process, the size (area) of the unit cell can be reduced to about several μm by several μm to several tens of μm by several tens of μm. On the other hand, a semiconductor wafer area limits the area of the maximum unit cell. A wafer having a diameter of 6 inches allows the unit cell to have the area of about 25 mm by 25 mm.

Third Embodiment

Simultaneous integration of a signal processing circuit to the formation of a humidity sensor on the semiconductor substrate enables production of a semiconductor integrated circuit in which the humidity sensor is incorporated in 1 chip.

In general, on the integrated circuit on the semiconductor substrate, a thick nitride film having a thickness of about 1 μm is diposed as a protective film. The nitride film is formed on a surface of the semiconductor substrate by a chemical vapor deposition (CVD) apparatus. When the integrated circuit and the electrode of the humidity sensor are integrated, the thick nitride film as a protective film having a thickness of about 1 μm is also coated onto the electrode of the humidity sensor. However, when the thick nitride film is coated, the capacitance C between the electrodes 11 and 12 shown in FIGS. 2A and 2B becomes equal to a series capacitance of CH and CN, where CH is a capacitance of the humidity sensitive film and CN is a capacitance of the nitride film, and the following equation (2) holds.

$$C=1/(1/C_H+2/C_N) \quad (2)$$

Where $$C_H=\epsilon_0 \cdot \epsilon_H \cdot S/d_H, \quad C_N=\epsilon_0 \cdot \epsilon_N \cdot S/d_N$$

In this case, $\epsilon_0$ is the permittivity of vacuum, $\epsilon_H$ is a dielectric constant of the humidity sensitive film, $\epsilon_N$ is a dielectric constant of a nitride film, S is an area where the electrodes 11 and 12 are opposing each other, $d_H$ is a thickness of the humidity sensitive film incorporated between the electrodes 11 and 12, and $d_N$ is a thickness of the nitride film on the surface of the electrodes 11 and 12. When the thickness $d_N$ of the nitride film is sufficiently small, $C_H$ is much smaller than $C_N$, Equation (2) thus becomes substantially the same as Equation (1). As is apparent from Equation (2), the smaller the thickness $d_N$ of the nitride film is, the larger the change in capacitance between the electrodes with respect to the humidity.

Accordingly, it is preferable that the protective film of FIGS. 2A and 2B is thin. It is therefore necessary that the thick nitride film is deposited once, then the thick nitride film is etched for the electrode portion, and a thin nitride film is deposited again on the electrode portion.

On the other hand, in the sectional view of FIG. 2B in the first embodiment, a barrier layer (hereinafter, referred to as barrier metal) is not illustrated under the metal wiring layer. In general, however, in order to enhance adhesion properties between the metal wiring layer and the insulating film thereunder, the barrier metal is coated in the semiconductor process. As the barrier metal, titanium nitride (TiN) and tantalum nitride (TaN) are known.

Figure 4A:
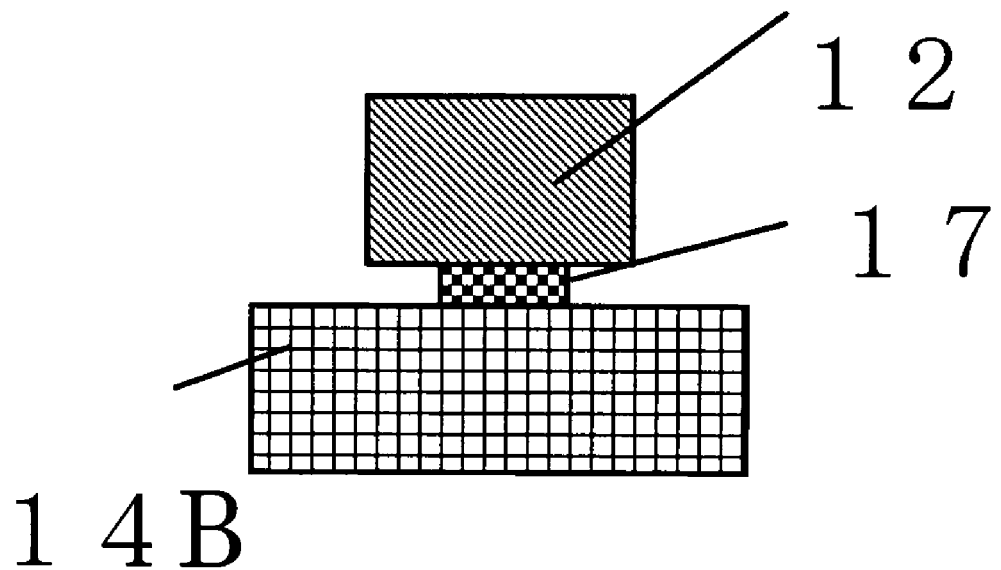
FIGS. 4A and 4B each are a sectional view of the electrode after a thick nitride film is etched.
Figure 4B:
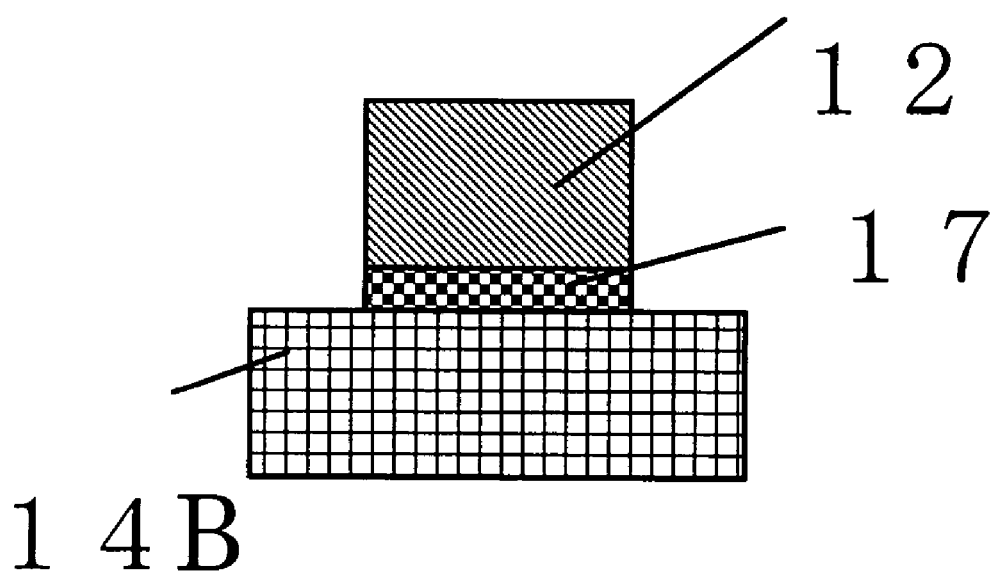

When a metal containing a large amount of nitride is used for the barrier metal, a barrier metal 17 is etched at the same time as shown in FIG. 4A in removal of the thick nitride film. As a result, adhesion properties between the metal wiring layer 12 and the underlying insulating film 14B deteriorates, which causes easy peeling-off of the metal wiring layer 12. For example, in a case of TiN, the ratio of the content of titanium and nitrogen is 1:1 in terms of the atomic weight, and the barrier metal 17 is also etched at the time of etching the thick nitride film. On the other hand, in a case where a metal containing a small amount of nitrogen (containing 10% or lower of nitrogen in terms of the atomic weight) is used for the barrier metal, the barrier metal 17 is hardly etched when etching the thick nitride film as shown in FIG. 4B. Therefore, adhesion properties between the metal wiring layer 12 and the insulating film 14B thereunder is not impaired.

In FIG. 1, the basic unit cells are arranged in the 5×5 grid pattern. However, the present invention can apparently provide the same effect irrespective of the number of the unit cells when a plurality of unit cells is arranged.

What is claimed is:

1. A humidity sensor comprising:
   a substrate;
   a first insulating film formed over the substrate;
   a first metal wiring layer disposed over the first insulating film;
   a second insulating film formed over the first metal wiring layer;
   a second metal wiring layer disposed over the second insulating film and formed with a plurality of unit cells, each comprising a first electrode and a second electrode which separately encompasses the first electrode in its entirety so as to have a capacitance between the first and second electrodes, and the first electrode being in electrical contact with the first metal wiring layer through the second insulating film; and
   a humidity sensitive film formed over the first electrode and the second electrode.

2. A humidity sensor according to claim 1, wherein the substrate comprises a semiconductor substrate.

3. A humidity sensor according to claim 1, wherein each of the plurality of unit cells has a silicon nitride film as a protective film.

4. A humidity sensor according to claim 1, wherein the first electrode and the second electrode have a barrier layer thereunder which contains less than 10% of nitrogen in terms of an atomic weight.

5. A humidity sensor according to claim 1, wherein a capacitance of each of the unit cells can be measured.

6. A humidity sensor according to claim 1, wherein the plurality of unit cells are formed as a grid pattern.

7. A humidity sensor according to claim 1, wherein the first electrode is in the shape of a square and the second electrode squarely encompasses the first electrode.

8. A humidity sensor according to claim 1, wherein the first and second electrodes are shaped as projections which are interdigitized.

9. A semiconductor device, comprising:
the humidity sensor according to claim 1; and
an integrated circuit including a signal processing circuit, wherein the humidity sensor and the integrated circuit are disposed on the substrate.

10. A semiconductor device according to claim 9, further comprising a silicon nitride film as a protective film.

11. A semiconductor device according to claim 10, wherein the silicon nitride film on the integrated circuit is thicker than the silicon nitride film on the humidity sensor.

* * * * *